(12) United States Patent
Sharabani et al.

(10) Patent No.: US 12,263,090 B2
(45) Date of Patent: Apr. 1, 2025

(54) ADJUSTABLE IMPLANT

(71) Applicant: SeaSpine, Inc., Carlsbad, CA (US)

(72) Inventors: Netanel Sharabani, Rishpon (IL); Oded Loebl, Tel Mond (IL); Didier Toubia, Raanana (IL)

(73) Assignee: SeaSpine, Inc., Carlsbad, CA (US)

( * ) Notice: Subject to any disclaimer, the term of this patent is extended or adjusted under 35 U.S.C. 154(b) by 354 days.

(21) Appl. No.: 17/713,612

(22) Filed: Apr. 5, 2022

(65) Prior Publication Data

US 2022/0226123 A1 Jul. 21, 2022

Related U.S. Application Data

(63) Continuation of application No. 16/592,970, filed on Oct. 4, 2019, now Pat. No. 11,298,239, which is a
(Continued)

(51) Int. Cl.
*A61F 2/44* (2006.01)
*A61B 17/88* (2006.01)
*A61B 17/56* (2006.01)
*A61F 2/30* (2006.01)
*A61F 2/46* (2006.01)

(52) U.S. Cl.
CPC .......... *A61F 2/442* (2013.01); *A61B 17/8858* (2013.01); *A61F 2/44* (2013.01); *A61F 2/4455* (2013.01); *A61F 2/447* (2013.01); *A61B 17/56* (2013.01); *A61F 2002/30405* (2013.01); *A61F 2002/30471* (2013.01); *A61F 2002/30507* (2013.01); *A61F 2002/30538* (2013.01); *A61F 2002/30556* (2013.01); *A61F 2/4611* (2013.01)

(58) Field of Classification Search
CPC .................... A61F 2/4455; A61F 2/447; A61F 2002/30556; A61F 2002/30538; A61F 2002/30537
See application file for complete search history.

(56) References Cited

U.S. PATENT DOCUMENTS 8,777,993 B2 7/2014 Siegal et al.
9,795,493 B1 * 10/2017 Bannigan .............. A61F 2/4455
(Continued)

FOREIGN PATENT DOCUMENTS

WO 2016063283 A1 4/2016

*Primary Examiner* — Eduardo C Robert
*Assistant Examiner* — Michelle C Green
(74) *Attorney, Agent, or Firm* — Dinsmore & Shohl LLP

(57) ABSTRACT

An adjustable implant includes a telescopic body with first and second portions in sliding engagement, and a deflectable linkage formed from a first linking segment, an intermediate segment and a second linking segment pivotally interconnected so that adjustment of a length of the telescopic body causes a corresponding deflection of the deflectable linkage. The first linking segment and the second linking segment are formed with projecting features that provide a partial gear engagement between the first and second linking segments such that, during adjustment of a length of the telescopic body and corresponding deflection of the deflectable linkage, pivotal motion of the first and second linking segments relative to the intermediate segment about the first and second pivot axes occurs in a fixed ratio defined by the partial gear engagement.

20 Claims, 11 Drawing Sheets

Related U.S. Application Data continuation of application No. 15/520,083, filed as application No. PCT/IL2015/051039 on Oct. 21, 2015, now Pat. No. 10,433,972.

(60) Provisional application No. 62/066,430, filed on Oct. 21, 2014.

(56) References Cited

U.S. PATENT DOCUMENTS

| | | |
|---|---|---|
| 10,433,972 B2 | 10/2019 | Sharabani |
| 11,298,239 B2 | 4/2022 | Sharabani |
| 2004/0193158 A1* | 9/2004 | Lim ................... A61B 17/025 606/99 |
| 2006/0241643 A1 | 10/2006 | Lim |
| 2011/0077738 A1 | 3/2011 | Ciupik et al. |
| 2012/0004732 A1* | 1/2012 | Goel .................... A61F 2/447 623/17.16 |
| 2012/0123546 A1* | 5/2012 | Medina ................ A61F 2/447 623/17.16 |
| 2013/0019087 A1 | 1/2013 | Osaki et al. |
| 2013/0190877 A1 | 7/2013 | Medina |
| 2014/0012383 A1 | 1/2014 | Triplett et al. |
| 2016/0100955 A1 | 4/2016 | Stinchfield |
| 2016/0324654 A1* | 11/2016 | Loebl .................. A61F 2/4465 |
| 2016/0331542 A1* | 11/2016 | Faulhaber ............ A61F 2/447 |
| 2017/0156885 A1* | 6/2017 | Zur ..................... A61F 2/4611 |
| 2017/0319352 A1* | 11/2017 | Dewey ................ A61F 2/447 |

\* cited by examiner

ADJUSTABLE IMPLANT

FIELD AND BACKGROUND OF THE INVENTION

The present invention relates to surgical implants and, in particular, it concerns an adjustable implant including a telescopic body.

It is known to employ adjustable implants which may be inserted into the body and then expand or otherwise change shape to assume a final shape. The present invention relates primarily, although not exclusively, to a subset of such devices in which the implant includes a telescopic body. i.e., where a body includes first and second portions which undergo relative motion towards and/or away from each other so that a length of the telescopic body can be varied.

SUMMARY OF THE INVENTION

The present invention is an adjustable implant.

According to the teachings of the present invention there is provided, an adjustable implant comprising: (a) a telescopic body comprising a first portion and a second portion, the first and second portions being in sliding engagement such that a length of the telescopic body is adjustable from a first length to a second length; and (b) a deflectable linkage comprising a first linking segment, an intermediate segment pivotally connected to the first linking segment about a first pivot axis, and a second linking segment pivotally connected to the intermediate segment about a second pivot axis, the first linking segment being pivotally connected to the first portion and the second linking segment being pivotally connected to the second portion such that adjustment of a length of the telescopic body causes a corresponding deflection of the deflectable linkage, wherein the first linking segment and the second linking segment are formed with projecting features configured to provide a partial gear engagement between the first and second linking segments such that, during adjustment of a length of the telescopic body and corresponding deflection of the deflectable linkage, pivotal motion of the first and second linking segments relative to the intermediate segment about the first and second pivot axes occurs in a fixed ratio defined by the partial gear engagement, and wherein the telescopic body and the deflectable linkage form at least part of an implant for deployment within a human body.

According to a further feature of an embodiment of the present invention, the projecting features define a gear tooth engaged in a complementary gear trough.

According to a further feature of an embodiment of the present invention, the partial gear engagement is configured such that pivotal motion of the first and second linking segments relative to the intermediate segment occurs equally and oppositely.

There is also provided according to the teachings of an embodiment of the present invention, an adjustable implant comprising: (a) a body having a length; (b) a deflectable linkage comprising a first linking segment, an intermediate segment pivotally connected to the first linking segment about a first pivot axis, and a second linking segment pivotally connected to the intermediate segment about a second pivot axis, the first linking segment being pivotally connected to the body about a third pivot axis and the second linking segment being pivotally connected to the body about a fourth pivot axis; and (c) a mechanism for adjusting a distance between the third and fourth pivot axes, thereby causing deflection of the deflectable linkage, wherein the first linking segment and the second linking segment are formed with projecting features configured to provide a partial gear engagement between the first and second linking segments such that, during adjustment of the distance between the third and fourth pivot axes, pivotal motion of the first and second linking segments relative to the intermediate segment about the first and second pivot axes occurs in a fixed ratio defined by the partial gear engagement, and wherein the body and the deflectable linkage form at least part of an implant for deployment within a human body.

According to a further feature of an embodiment of the present invention, the mechanism for adjusting a distance between the third and fourth pivot axes comprises a screw actuated mechanism for adjusting a length of the body.

According to a further feature of an embodiment of the present invention, the mechanism for adjusting a distance between the third and fourth pivot axes comprises a telescopic adjustment mechanism for adjusting a length of the body.

According to a further feature of an embodiment of the present invention, the projecting features define a gear tooth engaged in a complementary gear trough.

According to a further feature of an embodiment of the present invention, the partial gear engagement is configured such that pivotal motion of the first and second linking segments relative to the intermediate segment occurs equally and oppositely.

There is also provided according to the teachings of an embodiment of the present invention, an adjustable implant comprising: (a) a telescopic body comprising a first portion and a second portion, the first and second portions being in sliding engagement such that a length of the telescopic body is adjustable from a first length to a second length; and (b) a deflectable linkage comprising at least two interconnected segments including a first end segment and a second end segment, the first end segment being in articulated connection with the first portion and the second end segment being in articulated connection with the second portion such that adjustment of a length of the telescopic body causes a corresponding deflection of the deflectable linkage, wherein the first portion and the second end segment are formed with complementary cooperating surfaces shaped such that, during adjustment of a length of the telescopic body and corresponding deflection of the deflectable linkage, relative motion of the first portion and the second end segment maintains the cooperating surfaces in strain-limiting proximity, and wherein the telescopic body and the deflectable linkage form at least part of an implant for deployment within a human body.

According to a further feature of an embodiment of the present invention, the cooperating surfaces are configured to avoid contact in an unstressed form of the implant.

According to a further feature of an embodiment of the present invention, the cooperating surface of the second end segment includes a convexly curved bulge.

According to a further feature of an embodiment of the present invention, each of the first end segment and the second end segment is pivotally interconnected with an intermediate segment so as to be pivotable relative to the intermediate segment about respective first and second spaced-apart pivot axes.

According to a further feature of an embodiment of the present invention, the intermediate segment is formed with a tissue contact surface that extends along more than half a maximum length of the telescopic body.

According to a further feature of an embodiment of the present invention, the first end segment and the second end segment are interconnected so as to be relatively pivotable about a pivot axis.

According to a further feature of an embodiment of the present invention, the first end segment is formed with a tissue contact surface that extends along more than half a maximum length of the telescopic body.

There is also provided according to the teachings of an embodiment of the present invention, an adjustable implant comprising: (a) a telescopic body comprising a first portion and a second portion, the first and second portions being in sliding engagement such that a length of the telescopic body along an axis of the telescopic body is adjustable; and (b) a headless bolt deployed in a region of overlap between the first and second portions, the headless bolt having a threaded outer surface and having first end and second end abutment surfaces, wherein the first portion is formed with entrapment features configured to abut at least one of the first end and second end abutment surfaces of the bolt so as to prevent displacement of the bolt relative to the first portion in at least one direction along the axis, and wherein the second portion is formed with at least one elongated threaded surface deployed to engage the threaded outer surface of the bolt, the elongated threaded surface having a length greater than a length of the headless bolt, and wherein the telescopic body forms at least part of an implant for deployment within a human body.

According to a further feature of an embodiment of the present invention, a length of the headless bolt is less than the range of adjustment.

According to a further feature of an embodiment of the present invention, the length of the elongated threaded surface is sufficient to span a range of adjustment corresponding to a difference between a first length and a second length of the telescopic body.

According to a further feature of an embodiment of the present invention, the at least one elongated threaded surface is implemented as at least two elongated threaded surfaces deployed to engage spaced-apart regions of the threaded outer surface of the bolt.

According to a further feature of an embodiment of the present invention, the sliding engagement of the first and second portions is defined by sliding abutment surfaces of the first portion including two inward-facing walls, and sliding abutment surfaces of the second portion that are provided together with the elongated threaded surfaces by surfaces of two elongated projections, the elongated projections being shaped and sized to span a gap between the inward-facing walls and the threaded outer surface of the bolt.

According to a further feature of an embodiment of the present invention, the first portion includes two elongated projections carrying the entrapment features.

According to a further feature of an embodiment of the present invention, there is also provided a deflectable linkage comprising at least two interconnected segments including a first end segment and a second end segment, the first end segment being in articulated connection with the first portion and the second end segment being in articulated connection with the second portion such that adjustment of a length of the telescopic body causes a corresponding deflection of the deflectable linkage.

According to a further feature of an embodiment of the present invention, the deflectable linkage further comprises an intermediate segment, deflection of the deflectable linkage resulting in a change in spacing between the intermediate segment and the telescopic body.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1A:
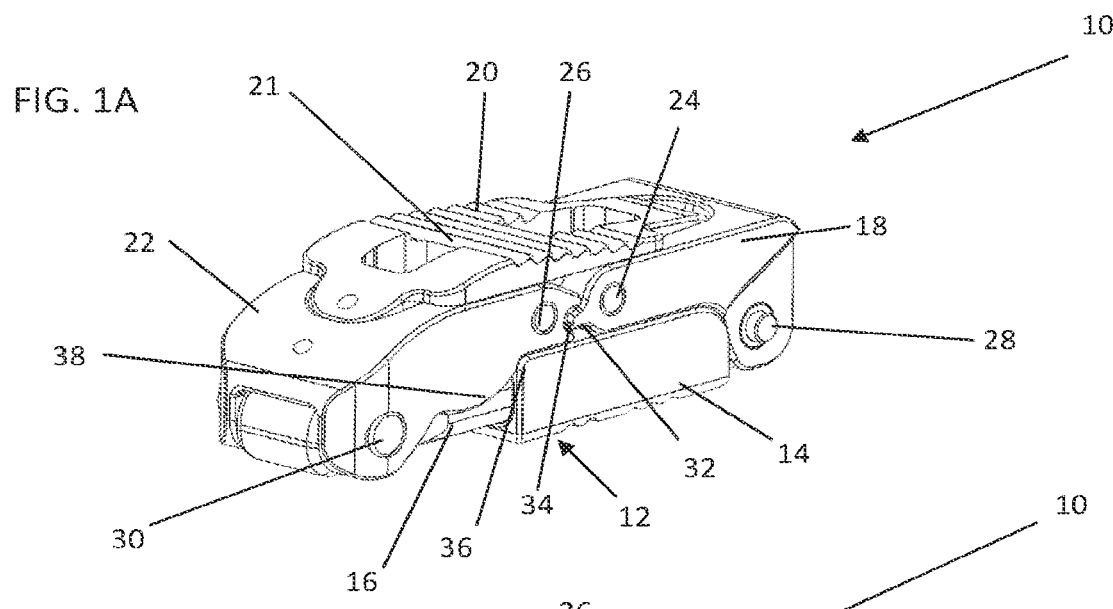
FIGS. 1A-1C are isometric views of an adjustable implant, constructed and operative according to a first embodiment of the present invention, shown in a collapsed state, a semi-deployed state, and a fully deployed state, respectively.
Figure 1B:
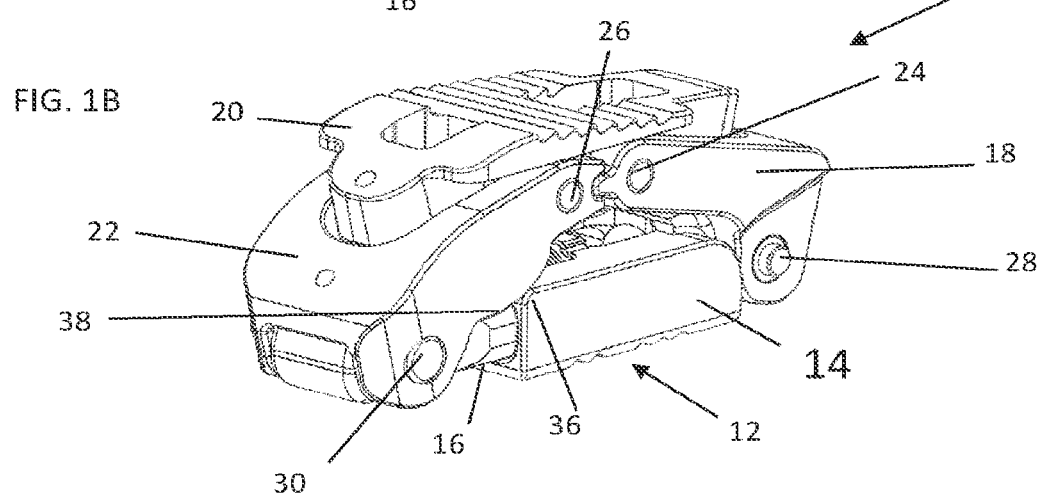
Figure 1C:
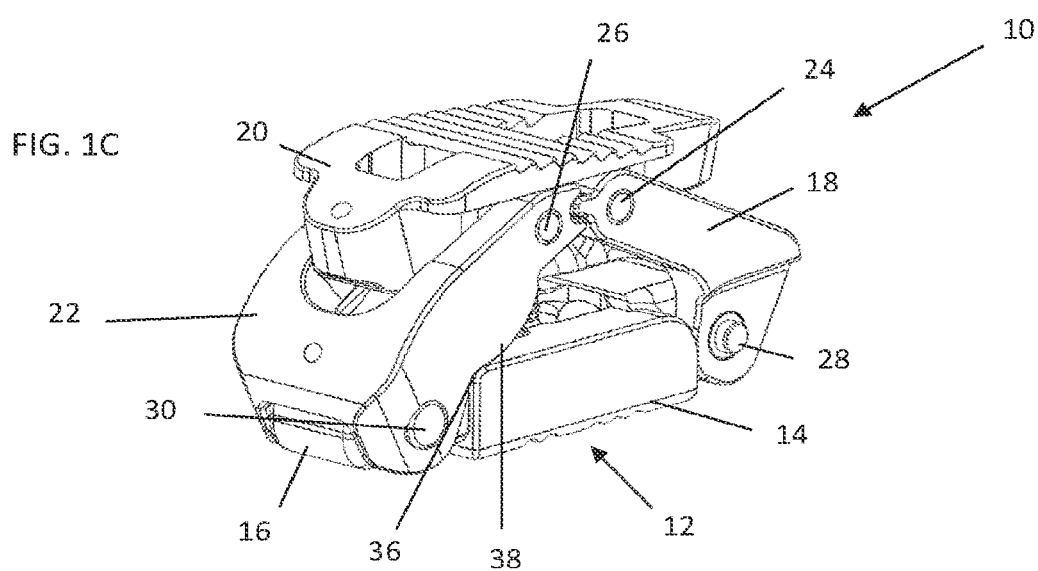

The present invention is an adjustable implant.

The principles and operation of adjustable implants according to the present invention may be better understood with reference to the drawings and the accompanying description.

By way of introduction before addressing the drawings in detail, the present invention encompasses a number of points of novelty which are exemplified by the various embodiments disclosed herein, but which each have utility independently in a range of other implementations and applications. For example, the embodiments of FIGS. 1A-8 illustrate a first aspect of the present invention which provides a gear-like mechanical engagement between links of a four-pivot-axis adjustable implant structure to define the adjustment motion. The embodiments of FIGS. 1A-6D and 9A-10 illustrate a second aspect of the present invention according to which complementary cooperating surfaces distinct from the articulating joints of an adjustable implant are shaped and positioned such that they provide additional support under conditions of loading of the implant to oppose the resulting strain. A third aspect of the present invention exemplified in the various illustrated embodiments relates to a mechanism for adjusting the length of a telescopic body, and hence adjusting the state of the implant. It should be noted that the first and second aspects of the invention may equally be implemented in adjustable implants which employ adjustment mechanisms other than the telescopic adjustment of the second aspect of the present invention, and that the telescopic body adjustment mechanism may be used in any or all implants which change their length, without requiring the features of the other aspects of the invention, and in some cases, without the presence of any deflectable linkage of the types to which the other aspects of the invention apply.

Referring now to the drawings. FIGS. 1A-6D illustrate a first embodiment of an adjustable implant, generally designated 10, illustrative of certain aspects of the present invention.

Figure 5A:
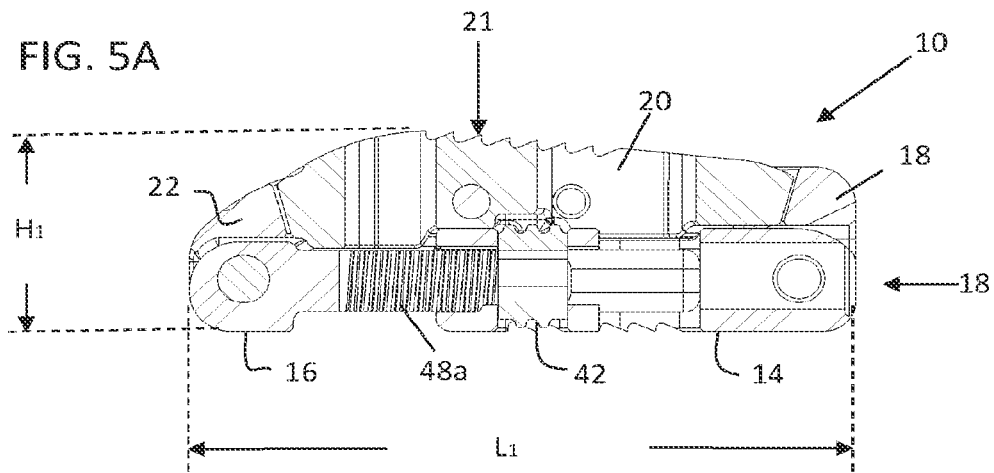
FIGS. 5A-5C are cross-sectional views taken along the line A-A in FIG. 4C, the adjustable implant being shown in a collapsed state, a semi-deployed state, and a fully deployed state, respectively.
Figure 5B:
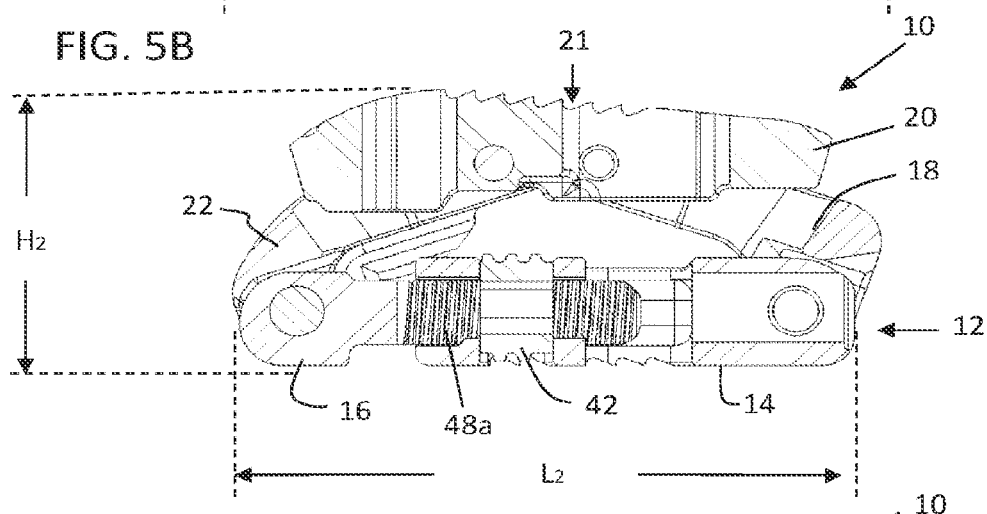
Figure 5C:
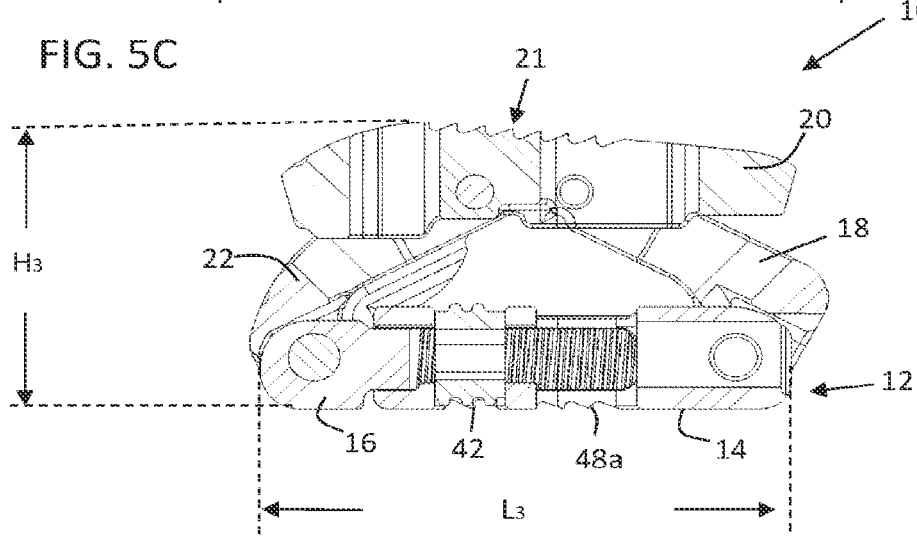
Figure 6A:
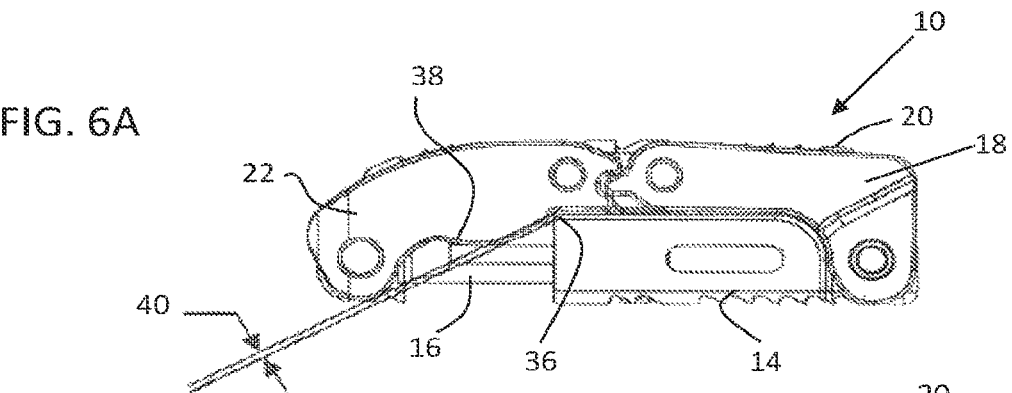
FIGS. 6A-6D are side views of the adjustable implant of FIGS. 1A-1C in a collapsed state, two intermediate positions, and a fully deployed state, respectively, illustrating a strain-limiting configuration according to an aspect of the present invention.
Figure 6B:
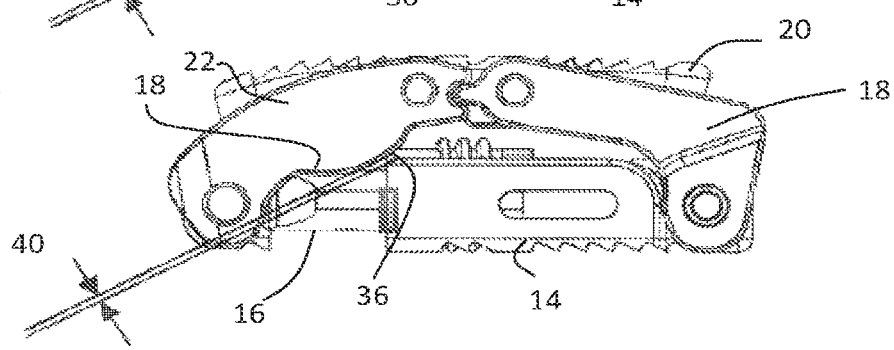
Figure 6C:
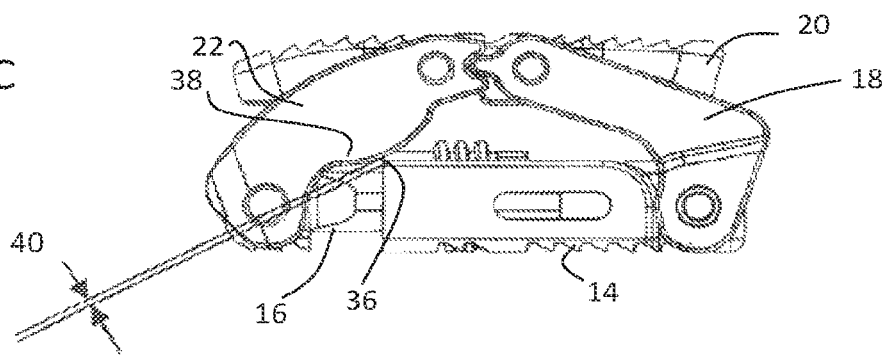
Figure 6D:
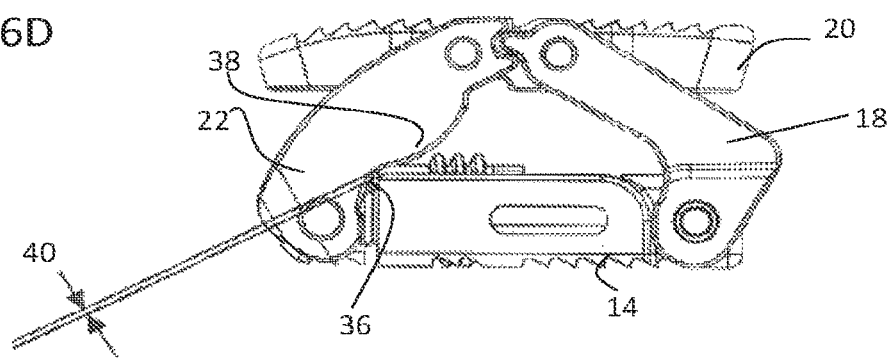

Adjustable implant 10 has a telescopic body 12 including a first portion 14 and a second portion 16. First and second portions 14 and 16 are in sliding engagement such that a length of the telescopic body is adjustable from a first length to a second length. In the embodiment shown, adjustable implant 10 also has a deflectable linkage including at least two, and in this case three, interconnected segments 18, 20 and 22 of which segment 18 is a first end segment (or "linking segment") in articulated connection with first portion 14 and segment 22 is a second end segment (or "linking segment") in articulated connection with second portion 16. The structure is such that adjustment of a length of the telescopic body causes a corresponding deflection of the deflectable linkage, as best illustrated in FIGS. 5A-5C where progressive decrease in the length of telescopic body 12 from $L_1$ through $L_2$ to $L_3$ causes progressive deflection of the deflectable linkage, in this case corresponding to parallel motion of the intermediate segment 20 away from telescopic body 12, to increase the height of implant 10 from an initial low-profile $H_1$ through $H_2$ to $H_3$.

Implant 10 of this example has four distinct pivotal connections each having one or more pivot pin whose central axis defines a distinct pivot axis: a first pivot axis 24 between first end segment 18 and intermediate segment 20; a second pivot axis 26 between intermediate segment 20 and second end segment 22; a third pivot axis 28 between first end segment 18 and first portion 14; and a fourth pivot axis 30 between second end segment 22 and second portion 16. (In the exploded view of FIG. 2, the corresponding openings for receiving the pivot pins are labeled with the corresponding numerals primed.) The distance between pivot axes 28 and 30 is adjustable, in this case by telescopic adjustment of telescopic body 12, so as to adjust the shape of the implant. However, a structure with rigid links interconnected at four pivot axes does not inherently define a unique geometry, and could in principle allow a rocking motion of intermediate segment 20 relative to telescopic body 12. A first aspect of the present invention addresses this issue by reducing the degrees of freedom of the four-pivot-axis so that rotation about two adjacent axes, in this case, axes 24 and 26 occurs in a fixed ratio, most preferably equal and opposite. This results in a stable and well-defined orientation of intermediate segment 20 at every stage of the adjustment process, providing, for example, parallel motion between telescopic body 12 and intermediate segment 20 as illustrated here.

Figure 4A:
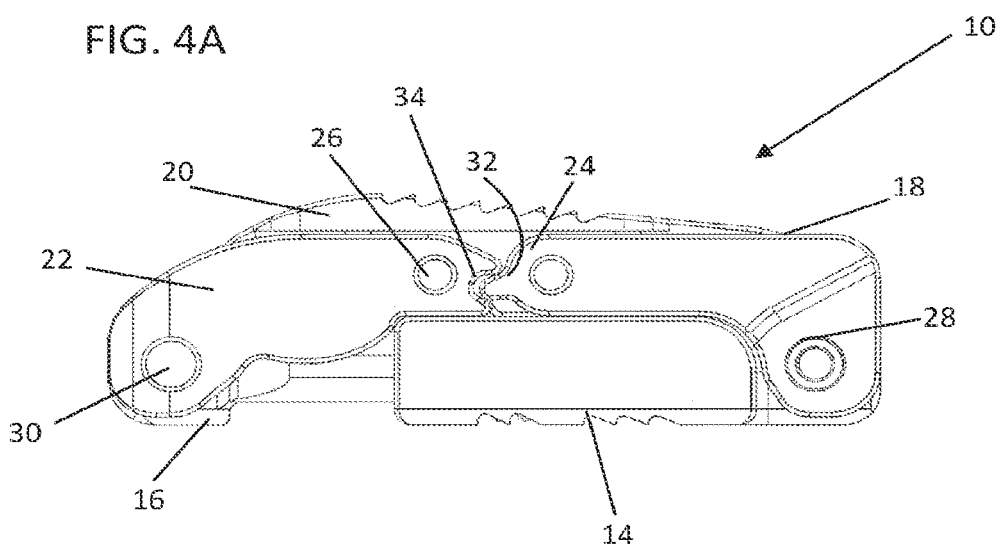
FIGS. 4A-4C are side, top and bottom views, respectively, of the adjustable implant of FIGS. 1A-1C.
Figure 4B:
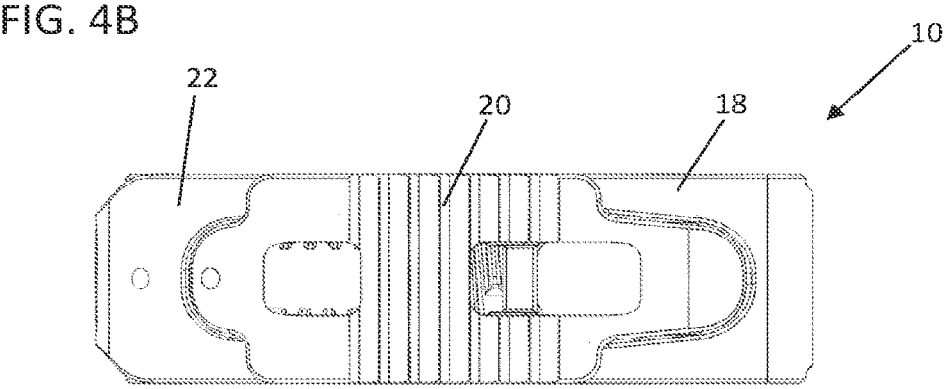
Figure 4C:
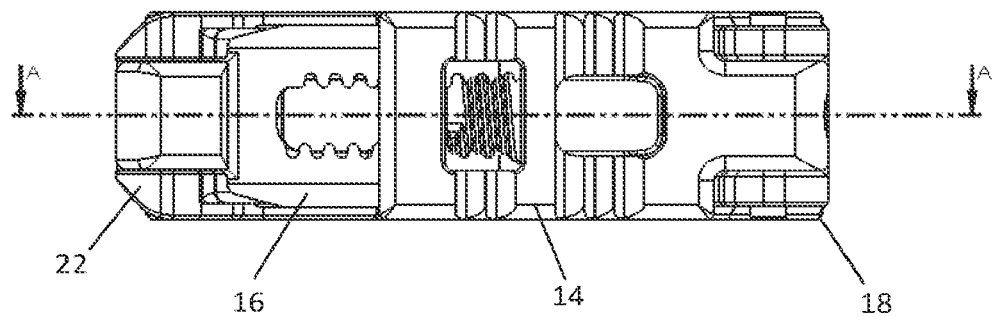
Figure 4D:
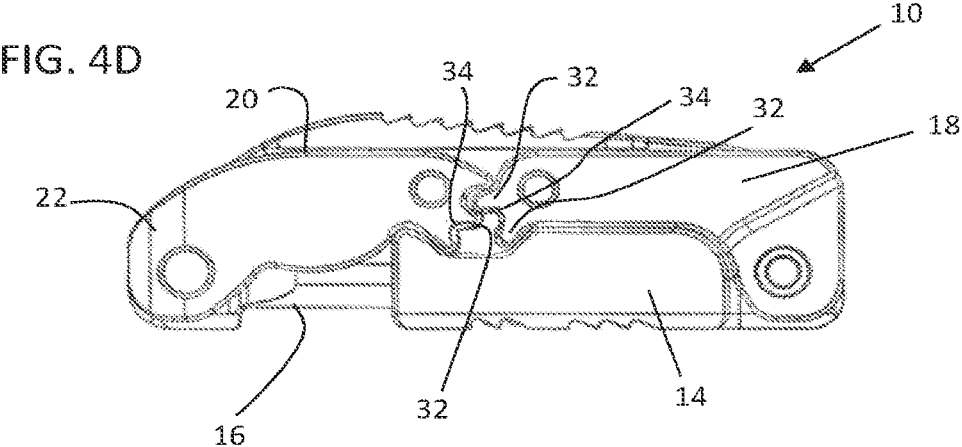
FIG. 4D is a view similar to FIG. 4A showing a variant implementation of a partial gear engagement between two linking segments of the implant.

Structurally, in the implementation illustrated here, first linking segment 18 and second linking segment 22 are formed with projecting features configured to provide a partial gear engagement between the segments. Specifically, in this case, first linking segment 18 is formed with a gear tooth 32 while second linking segment 22 is formed with projections defining therebetween a complementary tooth trough 34 for receiving gear tooth 32. Tooth 32 and trough 34 are preferably partial profiles of corresponding virtual gear wheels centered at pivot axes 24 and 26, respectively, and most preferably have standard involute gear geometry, as is well known in the field of gears. Given the limited range of angular motion of the implant from its collapsed state to its fully deployed state, in certain cases as illustrated here, it has been found sufficient to include a single gear tooth 32 and single corresponding inter-tooth trough 34. However, alternative implementations employ two or more teeth and associated troughs on one or both of the linking segments, for example, to provide reliable engagement for an implant with a larger range of angles and/or using smaller size teeth. By way of one further non-limiting example, FIG. 4D shows schematically a variant implementation in which the gear configuration is implemented with a plurality of teeth, specifically, two teeth 32 and one interposed trough 34 as part of segment 18 and two troughs 34 with one interposed tooth 32 as part of segment 22.

Although a conventional gear tooth shape is believed to be advantageous, it should be noted that alternative forms of "gear engagement" between the two linking segments may also be used. Various non-standard tooth shapes, or even a transverse pin (i.e., projecting parallel to the pivot axes) on one linking segment engaged in a slot extending radially from the pivot axis of the other linking segment, can provide a sufficiently good approximation to a fixed ratio of rotation between the two linking segments.

In the particular case illustrated here, the inter-axis lengths of linking segment 18 (between axes 24, 28) and linking segment 22 (between axes 26, 30) are equal, and the partial gear engagement employs tooth/trough profiles corresponding to virtual gears of the same sizes/angular pitch. As a result, the line between axes 24 and 26, corresponding to the orientation of intermediate segment 20, remains parallel to the length of telescopic body 12 (or a line joining axes 28 and 30). By employing linking segments of differing inter-axis lengths and/or by employing an asymmetric partial gear engagement, other desired geometries of motion can be achieved, such as various combinations of adjustable spacing and angle of inclination. In each case, however, the form of the motion is predefined by the structure, and the device is preferably stable against any rocking motion in each position over its range of motion.

This aspect of the present invention may be implemented in any implant in which the distance between axes 28 and 30 can be adjusted. Examples include any and all cases in which a screw (boll) is employed to adjust a length of a base/body between axes 28 and 30, and all forms of telescopic bodies, whether using an internal adjustment mechanism such as that described herein or whether adjusted by an external/removable actuator mechanism. Additionally, this aspect of the present invention may be implemented in cases where a base of the implant is of fixed length, but where an adjustment mechanism displaces one or both of pivot axes 28 and 30 along the base so as to vary a distance between them.

It will be noted that the aforementioned pivot axes do not necessarily correspond to the extremities of the corresponding segments. Particularly notable is that intermediate segment 20 is formed with a tissue contact surface 21 which, in particularly preferred implementations, extends along more than half a maximum length of the telescopic body. This tissue contact surface together with the outward-facing lower surface(s) of telescopic body 12 provide opposing contact surfaces which, on adjustment of the implant, can be used to push apart tissues to achieve a desired extent of separation, distraction or height restoration, all according to the particular application.

Turning now to a second aspect of the invention, this is applicable in cases where relative motion of parts of the body/base cause deflection of a deflectable linkage, such as the three-segment linkage of adjustable implant 10 or a two-segment linkage such as that of adjustable implant 200 described below. The motion of the adjustable implants described herein is primarily defined by the geometry of the pivot axes and adjustment of the telescopic body, optionally further defined by a partial gear arrangement according to the first aspect of the present invention described above. However, under conditions of significant applied loading, it may be preferable that part of the load is borne by structures other than the pivot connections.

To this end, in the example of adjustable implant 10, first portion 14 of telescopic body 12 and second end segment 22 of the deflectable linkage are formed with complementary cooperating surfaces shaped such that, during adjustment of a length of telescopic body 12 and corresponding deflection of the deflectable linkage, relative motion of first portion 14 and second end segment 22 maintains the cooperating surfaces in strain-limiting proximity. "Strain-limiting proximity" is used herein in the description and claims to refer to two components which are either in contact with each other or which are in proximity with each other to the extent that, when a load is applied to the implant sufficient to elastically deform the implant, the surfaces of the components come into contact within the range of elastic deformation. i.e., before the elastic limit of any of the components is exceeded. In certain particularly preferred embodiments, such contact occurs during the "initial stages" of elastic deformation which, for this purpose, may be defined as the first 50%, more preferably the first 10%, and most preferably the first 5%, of linear strain as a proportion of the maximum strain which would bring the implant to its elastic limit. In this manner, the complementary cooperating surfaces effectively serve as a "stop" to limit or resist elastic deformation of the implant, thereby improving the performance of the implant as a whole under conditions of loading. In certain alternative embodiments, an initial gap between the components in strain-limiting proximity may be chosen to be in excess of 50% of the maximum strain which would bring the implant to its elastic limit. This option may be particularly advantageous where it is desired to provide relatively high flexibility of the implant during routine loading while ensuring that the deformation "bottoms-out" and is stopped before approaching levels which might result in damage.

Structurally, this strain-limiting (deformation-limiting) feature is most preferably implemented as illustrated here by providing a small abutment surface or edge 36 at the extremity of first portion 14 and a convexly curved bulge 38 along a lower edge of second end segment 22. The shape of the convexly curved bulge is calculated (or empirically derived) to match the path of relative motion between second end segment 22 and edge 36 as the implant is adjusted through its range of motion, thereby ensuring that the desired proximity is maintained throughout the range. FIGS. 6A-6I) illustrate a sequence of states spanning the range of adjustment, and illustrate a clearance 40 which is preferably maintained according to certain implementations of the present invention between edge 36 and the adjacent region of bulge 38. This clearance as observed in the unstressed state of the implant is in certain preferred implementations small compared to the dimensions of the implant, typically amounting to no more than 10%, and more preferably 5%, of the overall dimension of the implant in the direction of the spacing, even in the collapsed state. This clearance preferably remains substantially constant over the range of adjustment of the implant, for example, most preferably varying by no more than ±20%. Provision of a small clearance in the unloaded state of the implant may be advantageous in that it ensures that the strain-limiting features do not add significant frictional resistance to a process of adjusting the implant shape, at least until a stage of deployment where significant loading is encountered. It may also provide a relatively high-flexibility state, as mentioned above.

Throughout the exemplary embodiments described herein, each of the "segments" described may be implemented as a unitary body, as a bilateral "forked" structure, or as a bilateral pair of separate elements which once assembled move in unison and are functionally equivalent to a single "segment". In adjustable implant 10 as illustrated here, first and second end (linking) segments 18 and 22 are forked elements which extend bilaterally on either side of intermediate segment 20 which is disposed internally to those segments. In the context of the strain-limiting features, it will be appreciated that these features may be provided on only one side of the forked second end segment 22 or, more preferably, on both sides thereof, thereby maximizing the structural support provided by these configurations under conditions of loading.

Figure 9A:
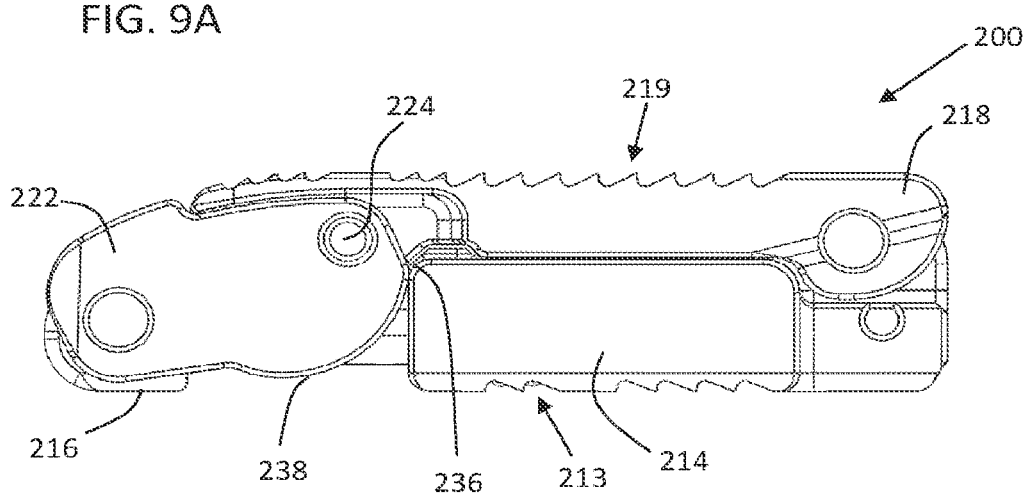
FIGS. 9A and 9B are side views of a further implementation of an adjustable implant, constructed and operative according to an embodiment of the present invention, shown in a collapsed state and a deployed state, respectively.
Figure 9B:
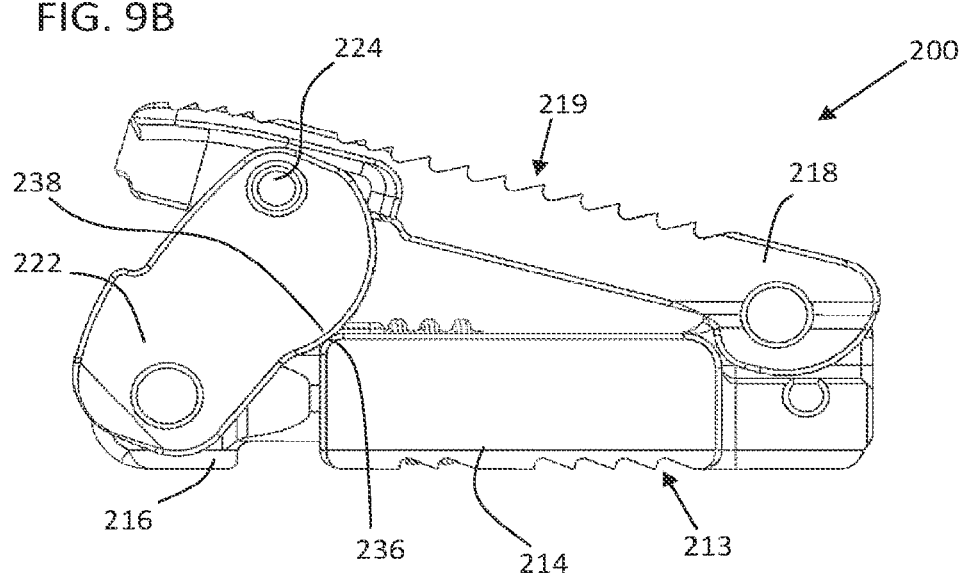
Figure 10:
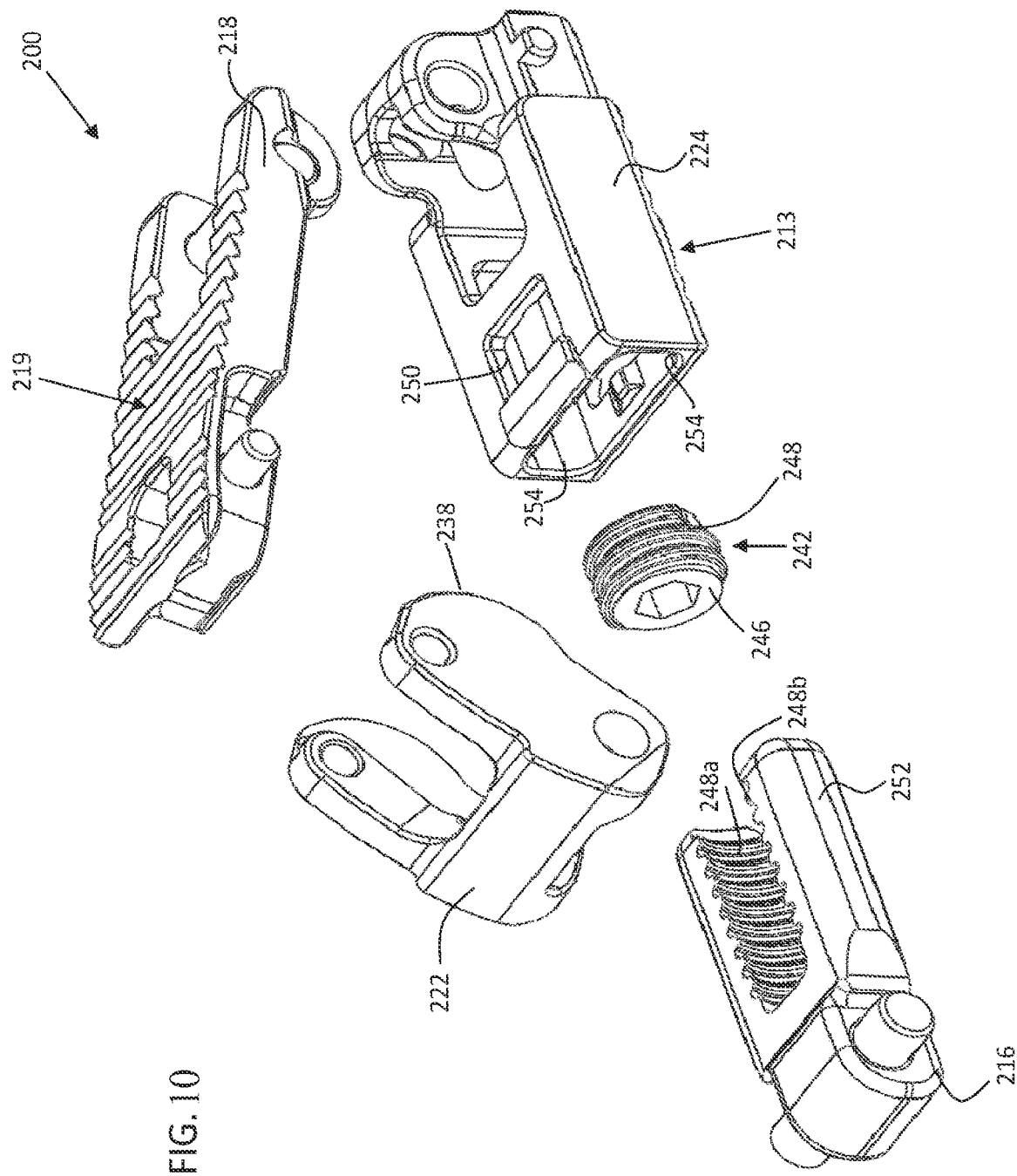
FIG. 10 is an exploded isometric view of the adjustable implant of FIGS. 9A and 9B.

The strain-limiting features according to this aspect of the present invention may be implemented in a range of different types of implant, and with a range of different adjustment mechanisms. By way of one further non-limiting example, FIGS. 9A-10 illustrate implementation of these features in the context of an adjustable-angle implant 200 in which a first end segment 218 and a second end segment 222 are interconnected so as to be relatively pivotable about a pivot axis 224. (Features of implant 200 that are analogous to features of implant 10 will be denoted by the same reference numerals with addition of 200 to the number.) First end segment 218 is preferably formed with a tissue contact surface 219 that extends along a major dimension having a length more than half a maximum length of a telescopic body formed by a first portion 214 and a second portion 216. The result is an implant which has an adjustable angle between tissue contact surface 219 and an outwardly facing tissue contact surface 213 of the telescopic base. In this context, the preferred implementation of adjustable-angle implant 200 as shown also includes strain-limiting features, structurally and functionally equivalent to those described above, including abutment surface or edge 236 and convexly-curved bulge 238. These and other features of implant 200 will be fully understood by analogy to the description of implant 10 above and from the further discussion of the structure and function of these implants described below.

Turning now to a third aspect of the present invention, the various embodiments of an adjustable implant illustrated herein also exemplify an adjustment mechanism for adjusting a length of a telescopic body which forms at least part of an implant. For conciseness of presentation, this aspect of the invention is illustrated herein in the context of an adjustable implant of implant 10, where a change in length of the telescopic body effects a change to a height of a deflectable linkage. It should be noted however that this aspect of the present invention may be used to advantage in any implant with telescopic adjustment, even if no such deflectable linkage is present, and may be used to advantage in applications in which an initially minimum-length implant is to be extended once within the body as well as application where an initially maximum-length implant is to be shortened within the body. The mechanism may also be useful in application where unidirectional actuation (i.e., just elongation or just shortening) without reversibility is sufficient.

Figure 2:
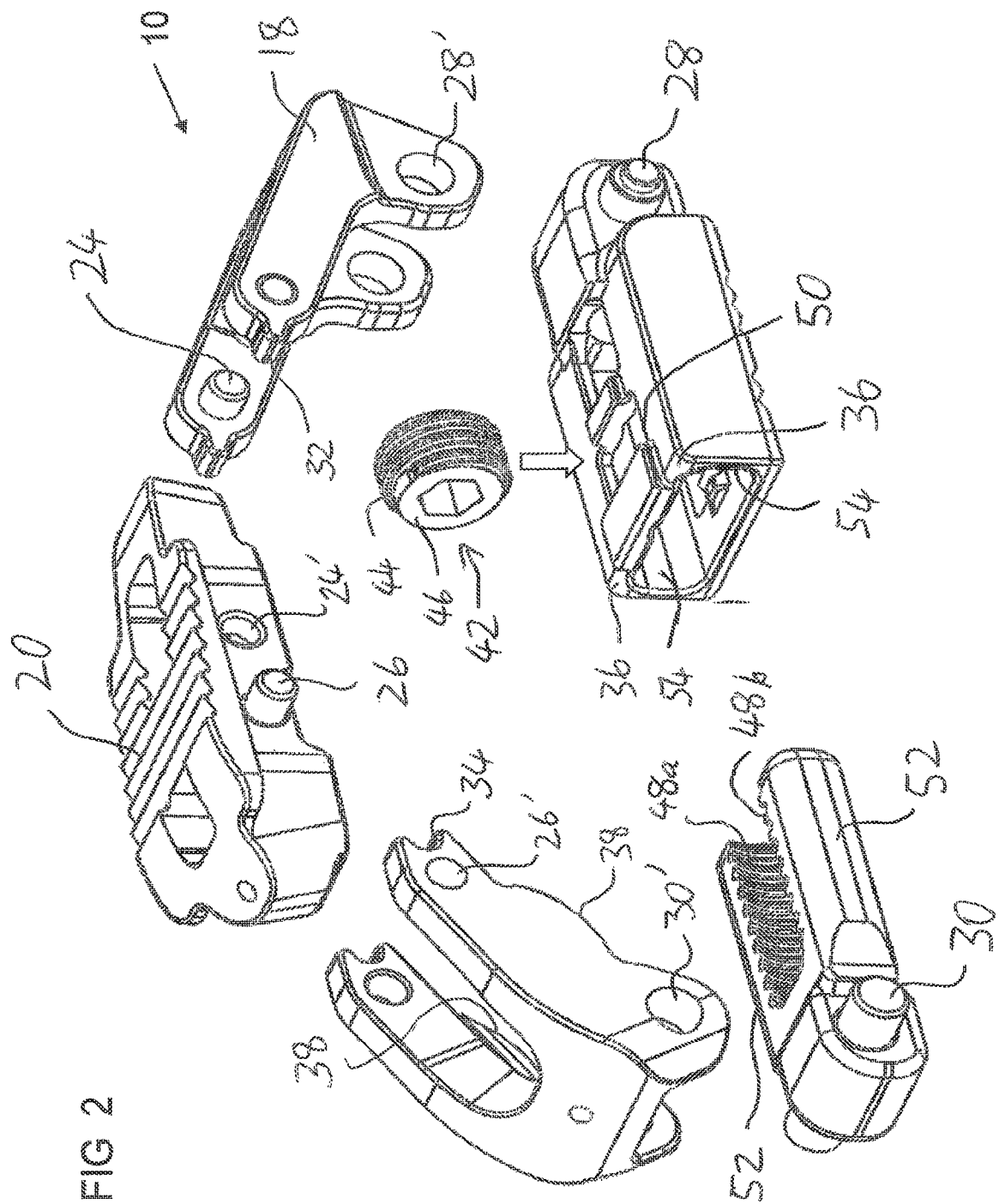
FIG. 2 is an exploded isometric view of the adjustable implant of FIGS. 1A-1C.
Figure 3:
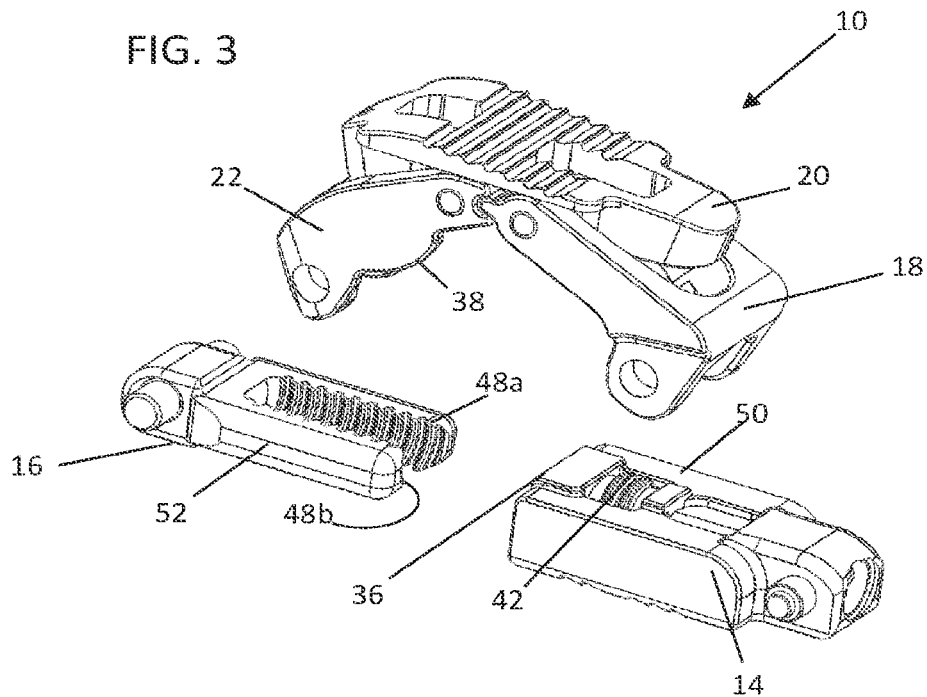
FIG. 3 is a partially assembled isometric view of the adjustable implant of FIGS. 1A-1C.

Referring now particularly to FIGS. 2 and 3, first and second portions 14 and 16 are here configured for sliding engagement such that a length of the telescopic body along an axis of the telescopic body is adjustable. A headless bolt 42, having a threaded outer surface 44 between two end abutment surfaces 46, is deployed in a region of overlap between the first and second portions. First portion 14 is formed with entrapment features configured to abut at least one, and preferably both, end abutment surfaces of bolt 42 so as to prevent displacement of bolt 42 relative to first portion 14 in at least one direction along the axis of the telescopic body. Second portion 16 is formed with at least one, and preferably two, elongated threaded surfaces 48a and 48b, deployed to engage the threaded outer surface of the bolt. Elongated threaded surfaces 48a and 48b have a length greater than a length of headless bolt 42.

In the non-limiting preferred example of implant 10, the entrapment features of first portion 14 include the upper and lower edges of a slot 50 into which bolt 42 is inserted during assembly, such that the upper and lower edges of the slot abut end abutment surfaces 46 to prevent axial displacement of the bolt relative to first portion 14. Rotation of bolt in that inserted position engages and draws inwards (or if reversed, forces outwards) elongated threaded surfaces 48a and 48b, thereby adjusting a length of telescopic body 12.

The term "headless bolt" is used herein to refer to a bolt which does not have a head of diameter greater than the threaded shaft of the bolt. In order to allow turning of bolt 42 to adjust the length of telescopic body 12, one of end abutment surfaces 46 is preferably formed with a shaped recess, which may be a shallow recess or a through-bore passing along the length of the bolt, to receive a correspondingly shaped tool tip.

The use of a "trapped" headless bolt 42 within first portion 14 and relatively long threaded surfaces 48a, 48b, allows the use of a bolt which in some embodiments is shorter than the range of adjustment of the device. This may provide certain advantages such as leaving a larger area available for openings through the implant, for example, to allow bone ingrowth through the implant. Where the bolt is relatively short, the range of adjustment of the telescopic body is typically defined primarily by the length of elongated threaded surfaces 48a, 48b, which preferably span the range of adjustment corresponding to a difference between a first length $L_1$ and a second length $L_3$ (FIGS. 5A-5C of telescopic body 12.

A range of implementations of the elongated threaded surface(s) may be used. In the particularly preferred non-limiting example of implant 10, the elongated threaded surfaces are integrated with elongated projections 52 which also define sliding abutment surfaces as part of the sliding engagement with first portion 14. Specifically, first portion 16 is here formed with two inward-facing walls 54. Outer surfaces of elongated projections 52 are configured to move in sliding engagement with inward-facing walls 54 to define the sliding engagement between first and second portions 14 and 16, while the inward-facing elongated threaded surfaces 48a, 48b engage threaded outer surface 44 of bolt 42. Elongated projections 52 are preferably shaped and sized to span a gap between inward-facing walls 54 and threaded outer surface 44 of bolt 42, such that contact between elongated projections 52 and walls 54 prevents any outward flexing of projections 52 and maintains reliable engagement of elongated threaded surfaces 48a, 48b with threaded outer surface 44 of bolt 42.

The operation of the adjustment mechanism can be best understood from FIGS. 5A-5C. In FIG. 5A, bolt 42 is engaged with the extremities of threaded surfaces 48a (and 48b), corresponding to the longest state $L_1$ of telescopic body 12 which, in this embodiment, is also the lowest height $H_1$ configuration for insertion into the body. A suitable tool (not shown) is then inserted along an access channel from the right side of telescopic body 12 as shown, and is used to turn bolt 42. As it turns, engagement of bolt 42 with threaded surfaces 48a (and 48b) draws second portion 16 towards first portion 14, as seen in the successive positions of FIGS. 5B and 5C. Longitudinal motion of bolt 42 relative to first portion 14 is prevented by the abutment of the ends of bolt 42 against the top and bottom edges of slot 50. In this example, as the length progressively decreases through $L_2$ to $L_3$, the deflectable linkage is progressively deflected to increasing heights of $H_2$ and $H_3$, until the end of the range of motion is reached, typically defined either by reaching the end of the thread or by reaching mechanical abutment, for example, of second portion 16 against first portion 14.

Figure 7A:
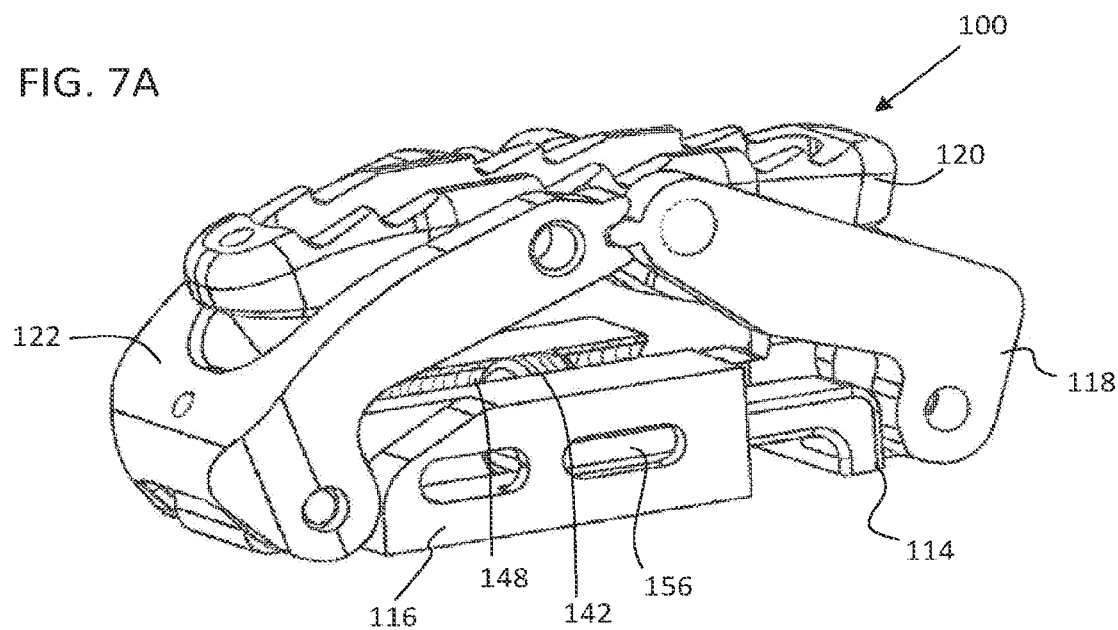
FIG. 7A is an isometric view of an alternative implementation of an adjustable implant, constructed and operative according to an embodiment of the present invention, shown in a semi-deployed state.
Figure 7B:
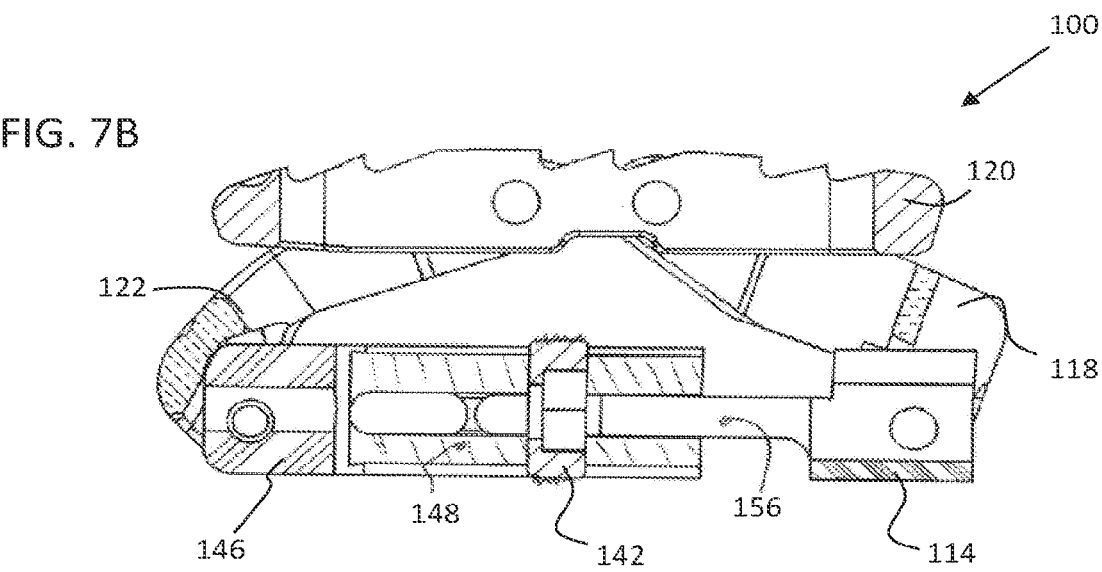
FIG. 7B is a center-plane cross-sectional view taken through the adjustable implant of FIG. 7A.
Figure 8:
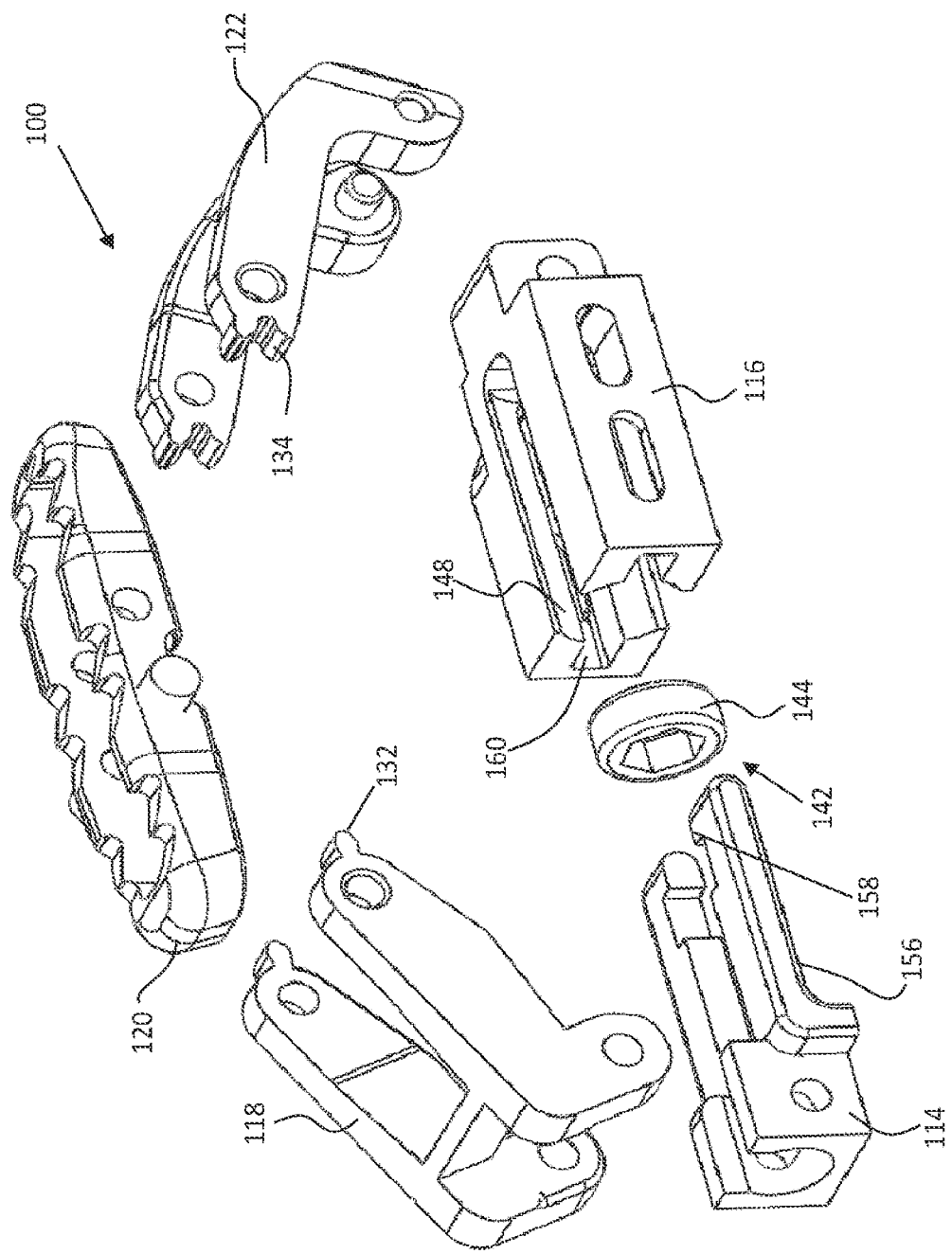
FIG. 8 is an exploded isometric view of the adjustable implant of FIG. 7A.

Turning now to FIGS. 7A-8, it should be noted that the trapped, headless bolt approach may be implemented using a wide range of different structures both for the entrapment features and for the elongated threaded surfaces. By way of one further non-limiting example, FIGS. 7A-8 illustrate an alternative implementation of an adjustable implant, generally designated 100, constructed and operative according to a further embodiment of the present invention. Implant 100 is generally analogous to implant 10 described above, and equivalent features are labeled with similar reference numerals incremented by 100.

In this case, first portion 114 includes two elongated projections 156 carrying entrapment features in the form of cut-outs 158 which provide surfaces abutting end abutment surfaces 146 of headless bolt 142. Second portion 116 in this case is formed as a block with inward-facing elongated threaded surfaces 148 that are subdivided by slots 160 which are shaped to receive projection 156. By positioning bolt 142 within cut-outs 158 and introducing the ends of elongated projections 156 into the beginnings of slots 160, threaded outer surface 144 is brought up against the start of elongated threaded surfaces 148 such that rotation of bolt 142 by a suitable tool (not shown) causes bolt 142 to draw second portion 116 and first portion 114 together. The remaining structural features and function of implant 100 will be understood by analogy to that of implant 10 described above.

Turning now to FIGS. 9A-10, these illustrate variable-angle implant 200 which was described above in the context of the strain-limiting features. As best seen in the exploded view of FIG. 10, the telescopic adjustment mechanism employed in this example is essentially identical to that of implant 10 described above, with equivalent elements labeled similarly with addition of 200 to the reference numerals.

Figure 11A:
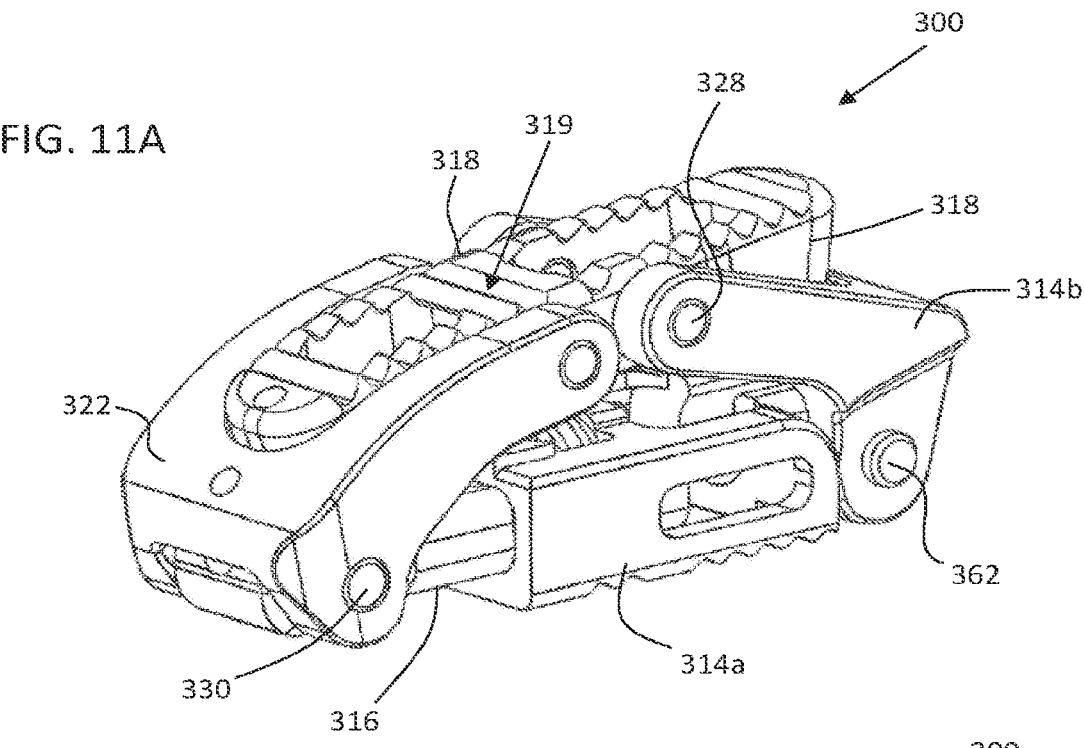
FIGS. 11A and 11B are isometric views of a further variant implementation of an adjustable implant, constructed and operative according to an embodiment of the present invention, shown in a collapsed state and a deployed state.
Figure 11B:
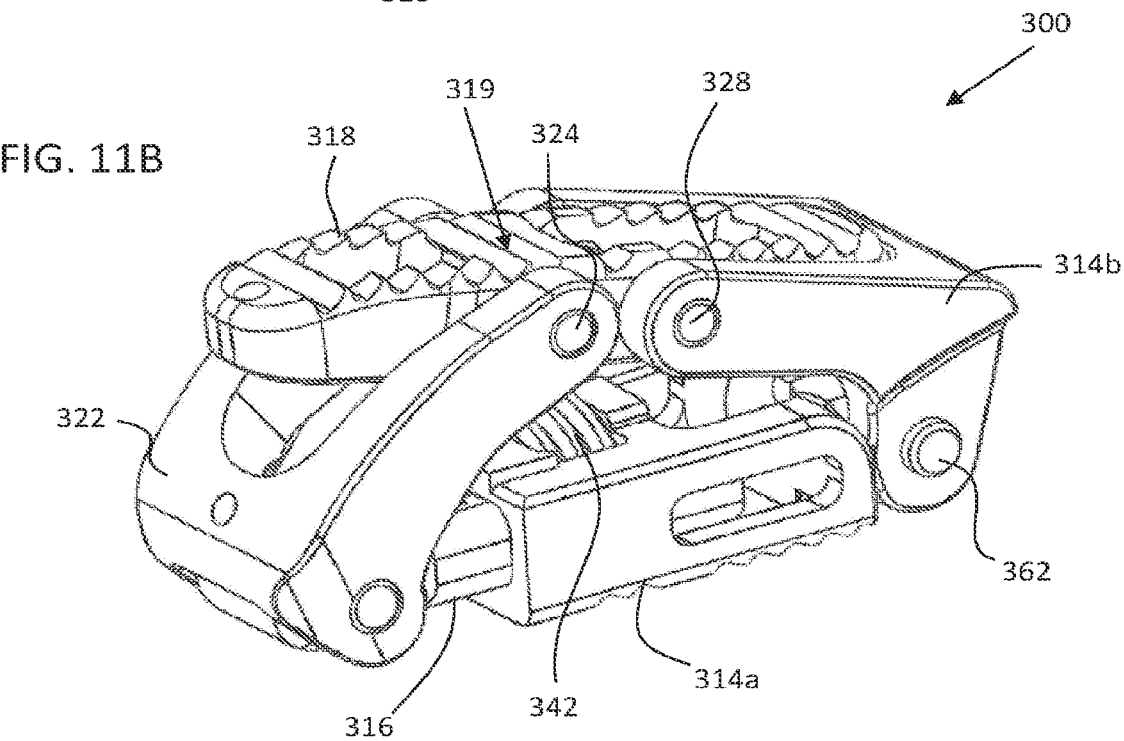

Turning now to FIGS. 11A and 11B, these illustrate a further embodiment of a variable-angle implant, generally designated 300. The structure and function of implant 300 are to a large extent analogous to that of implant 10 described above, and similar elements are designated by similar reference numerals with addition of 30) to the number.

Implant 300 is a variable-angle implant, functionally analogous to implant 200, but differs from implant 200 primarily in that the first portion of the telescopic body is here implemented as two rigidly interconnected or integrally formed sections 314a and 314b. (Projection 362 provides an anchor point for a delivery system (not shown) for the implant and is not a pivot.) The effect of this first portion structure is to position the pivotal connection 328 between first portion 314b and first end segment 318 in the mid-half (i.e., between 25% and 75%) of the maximum length of the implant, and in certain preferred implementations, at a relatively high position above an initial height of pivotal connection 324. This geometry facilitates a range of angles of tissue contact surface 319 which spans from a "negative angle" as shown in FIG. 11A to a "positive angle" as shown in FIG. 11B. The negative angle initial configuration may provide advantages in certain application during insertion of the implant into the body by providing a low profile leading end and a wedge-like overall profile for progressively separating tissues during insertion. Here too, the exemplary non-limiting adjustment mechanism for the telescopic body is essentially similar to that of implant 10 described above, and will not be described further.

All of the above exemplary embodiments are suitable for use, as is or with minor modifications that will be self-explanatory to a person of ordinary skill in the art, in a wide range of orthopedic applications, and especially in cases where a distance, spacing and/or angle between two tissue surfaces is to be increased or adjusted. One non-limiting field of particular relevance is spinal surgery, including devices for intra-body, inter-body placement within or between adjacent vertebral bodies. The devices are typically delivered in a low-profile form while held by an elongated holder (not shown), are inserted to the desired target location, and are then adjusted to provide the desired degree of tissue separation and/or angular correction. For intervertebral fusion applications, the devices may be used for any approach direction including, but not limited to, various posterior and lateral approach routes. Various bone-ingrowth openings (for example, as illustrated) are preferably provided to facilitate fusion and/or osteo-integration.

It should be noted that embodiments of the present invention which provide "parallel" adjustment of spacing between tissue contact surfaces do not necessarily, or even typically, have contact surfaces which are parallel per se. Thus, for example, an upper tissue contact surface 21 of implant 10 as best seen in FIGS. 5A-5C is shown with a preset incline to provide slight lordotic angle restoration in addition to an overall anatomically-rounded shape towards its extremities. Furthermore, the tissue contact surfaces are typically modified by various ridges, projection or other features to enhance mechanical anchoring against tissue surfaces, as well as openings as mentioned above.

The disclosed implants may be formed from any and all materials or combinations of materials known to be suitable for implementation of surgical implants. Examples include, but are not limited to, titanium, surgical stainless steel and polymers such as PEEK.

Except where stated otherwise, it should be noted that the various structures illustrated herein as being implemented on either a proximal or a distal end of an implant should be understood to be reversible. Thus, where features are described as being part of a first portion of the telescopic body or a first end segment of a deflectable linkage and are illustrated as being a proximal structure, these structures can readily be adapted for implementation at a distal end of the implant, and vice versa.

It will be appreciated that the above descriptions are intended only to serve as examples, and that many other embodiments are possible within the scope of the present invention as defined in the appended claims.

The invention claimed is:

1. A method of deploying an adjustable implant comprising the steps of:
   providing an adjustable implant having a deflectable linkage and a telescopic body, wherein the deflectable linkage includes at least two interconnected segments including a first linking segment and a second linking segment, wherein the telescopic body includes a first portion and a second portion, and wherein the first portion and the second linking segment are formed with complementary cooperating surfaces, wherein the first linking segment and the second linking segment are directly engaged by one or more corresponding projecting features;
   adjusting a length of the telescopic body from a first length to a second length;
   deflecting the deflectable linkage; and
   maintaining the complementary cooperating surfaces of the first portion and the second linking segment in strain-limiting proximity during adjustment of the length of the telescopic body and corresponding deflection of the deflectable linkage.

2. The method of claim 1 further comprising the step of sliding the first portion relative to the second portion when adjusting the length of the telescopic body.

3. The method of claim 1 further comprising the step of avoiding contact of the complementary cooperating surfaces when the implant is an unstressed form.

4. The method of claim 1 wherein each one of the first portion and the second linking segment includes two complementary cooperating surfaces.

5. The method of claim 1 wherein the deflectable linkage includes an intermediate segment, wherein each of the first linking segment and the second linking segment is pivotally interconnected with the intermediate segment.

6. The method of claim 1 wherein the cooperating surface of the second linking segment includes a convexly curved bulge.

7. The method of claim 1 further comprising the step of decreasing the length of the telescopic body increases a distance between a first contact surface of the telescopic body and a second contact surface of the deflectable linkage.

8. A method of deploying an adjustable implant comprising the steps of:
   providing an adjustable implant having a deflectable linkage further comprising a first linking segment and a second linking segment directly engaged by one or more corresponding projecting features and a telescopic body, wherein each of the deflectable linkage and the telescopic body comprises a complementary cooperating surface;
   deploying the implant from a collapsed state to a deployed state different from the collapsed state; and
   maintaining the complementary cooperating surfaces of the deflectable linkage and the telescopic body in strain-limiting proximity during deployment of the implant from the collapsed State to the deployed state.

9. The method of claim 8 wherein the cooperating surface of the deflectable linkage includes a convexly curved bulge.

10. The method of claim 8 further comprising the step of adjusting a length of the telescopic body.

11. The method of claim 10 further comprising the step of decreasing the length of the telescopic body increases a distance between a first contact surface of the telescopic body and a second contact surface of the deflectable linkage.

12. The method of claim 8 wherein the deflectable linkage includes at least two interconnected segments including the first linking segment and the second linking segment, wherein the telescopic body includes a first portion and a second portion, and wherein the first portion and the second linking segment are formed with the complementary cooperating surfaces.

13. The method of claim 12 wherein the deflectable linkage includes an intermediate segment, wherein each of the first linking segment and the second linking segment is pivotally interconnected with the intermediate segment.

14. The method of claim 12 wherein each one of the first portion and the second linking segment includes two complementary cooperating surfaces.

15. A method of deploying an adjustable implant comprising the steps of:
providing an adjustable implant having a deflectable linkage and a telescopic body, wherein the telescopic body includes a first portion and a second portion, wherein the deflectable linkage includes a first linking segment, an intermediate segment pivotally connected to the first linking segment about a first pivot axis, and a second linking segment pivotally connected to the intermediate segment about a second pivot axis, the first linking segment being pivotally connected to the first portion and the second linking segment being pivotally connected to the second portion, and wherein the first linking segment and the second linking segment are formed with projecting features configured to provide a partial gear engagement directly between the first linking segment and the second linking segment;
adjusting a length of the telescopic body from a first length to a second length;
deflecting the deflectable linkage; and
pivoting the first linking segment and the second linking segment relative to the intermediate segment about the first and second pivot axes occurs in a fixed ratio defined by the partial gear engagement.

16. The method of claim 15 wherein the projecting features define a gear tooth engaged in a complementary gear trough.

17. The method of claim 15 wherein the pivoting the first linking segment and the second linking segment relative to the intermediate segment occurs equally and oppositely.

18. The method of claim 15 wherein the telescopic body includes a first contact surface with a first tissue and the intermediate segment includes a second contact surface with a second tissue opposite to the first tissue, wherein decreasing the length of the telescoping body increases a distance between the first contact surface of the telescopic body and the second contact surface of the intermediate segment.

19. The method of claim 15 comprising the step of maintaining complementary cooperating surfaces of the first portion and the second linking segment in strain-limiting proximity during adjustment of the length of the telescopic body and corresponding deflection of the deflectable linkage.

20. The method of claim 19 wherein the complementary cooperating surface of the second linking segment includes a convexly curved bulge.

* * * * *